(12) United States Patent
Ono et al.

(10) Patent No.: US 9,962,094 B2
(45) Date of Patent: May 8, 2018

(54) VASCULAR ENDOTHELIAL FUNCTION INSPECTION APPARATUS

(71) Applicant: Nihon Kohden Corporation, Shinjuku-ku, Tokyo (JP)

(72) Inventors: Yoshinobu Ono, Tokyo (JP); Tsuneo Takayanagi, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 471 days.

(21) Appl. No.: 14/632,549

(22) Filed: Feb. 26, 2015

(65) Prior Publication Data
US 2015/0250394 A1 Sep. 10, 2015

(30) Foreign Application Priority Data

Mar. 6, 2014 (JP) ................................. 2014-044125

(51) Int. Cl.
*A61B 5/022* (2006.01)
*A61B 5/02* (2006.01)
*A61B 5/021* (2006.01)

(52) U.S. Cl.
CPC .......... *A61B 5/02007* (2013.01); *A61B 5/022* (2013.01); *A61B 5/02108* (2013.01); *A61B 5/02233* (2013.01)

(58) Field of Classification Search
CPC . A61B 5/02007; A61B 5/02108; A61B 5/022; A61B 5/02233
See application file for complete search history.

(56) References Cited

U.S. PATENT DOCUMENTS

| | | |
|---|---|---|
| 2006/0258944 A1 | 11/2006 | Takahashi et al. |
| 2008/0119741 A1 | 5/2008 | Friedman et al. |
| 2008/0214961 A1 | 9/2008 | Matsumoto et al. |

(Continued)

FOREIGN PATENT DOCUMENTS

| | | |
|---|---|---|
| EP | 2110074 A1 | 10/2009 |
| EP | 2606818 A1 | 6/2013 |

(Continued)

OTHER PUBLICATIONS

Cheung et al, Arterial Stiffness and Endothelial Function in Patients With Beta-Thalassemia Major, 2002, Circulation, 106(20): 2561-6.*

(Continued)

*Primary Examiner* — Christian Jang
*Assistant Examiner* — Angeline Premraj
(74) *Attorney, Agent, or Firm* — Sughrue Mion, PLLC

(57) ABSTRACT

A vascular endothelial function inspection apparatus includes a first cuff that is mounted to a first part of a subject, a cuff pressure control unit that controls a pressure applied to the first cuff, a pressure sensor that is connected to the first cuff, a cuff pressure detection unit that detects a cuff pressure from an output of the pressure sensor, a pulse wave detection unit that detects pulse waves from the output of the pressure sensor, a blood pressure measuring unit that measures a blood pressure value based on the cuff pressure and the pulse waves, a storage unit that stores therein an elasticity index value indicating an elasticity of a blood vessel of the subject, and an analysis unit that performs data processing for evaluating an endothelial function of the blood vessel.

16 Claims, 6 Drawing Sheets

(56) References Cited

U.S. PATENT DOCUMENTS

2009/0259131 A1    10/2009   Tsuji et al.
2011/0066048 A1    3/2011   Tsuji et al.
2013/0158419 A1    6/2013   Tsuji et al.

FOREIGN PATENT DOCUMENTS

| | | |
|---|---|---|
| JP | 2004129979 A | 4/2004 |
| JP | 2005168583 A | 6/2005 |
| JP | 2005205008 A | 8/2005 |
| JP | 2006115979 A | 5/2006 |
| JP | 2006296888 A | 11/2006 |
| JP | 2008212366 A | 9/2008 |
| JP | 2008289678 A | 12/2008 |
| JP | 2009388 A | 1/2009 |
| JP | 2009273870 A | 11/2009 |
| JP | 2011-056200 A | 3/2011 |
| JP | 2013126487 A | 6/2013 |

OTHER PUBLICATIONS

Extended European Search Report dated Aug. 18, 2015 by the European Patent Office in counterpart European Application No. 15156874.8.

Nemes et al: "Real-time three dimensional echocardiography for regional evaluation of aortic stiffness", European Journal of Echocardiography, Harcourt Publishers, Edinburgh, GB, vol. 8, No. 2, Jan. 18, 2007 (Jan. 18, 2007), pp. 161-162, XP005832217, ISSN: 1525-2167, DOI: 10.1016 J.EUJE. 2006.01.006.

Office Action dated Jun. 6, 2017, by the Japanese Patent Office in counterpart Japanese Application No. 2014044125.

\* cited by examiner

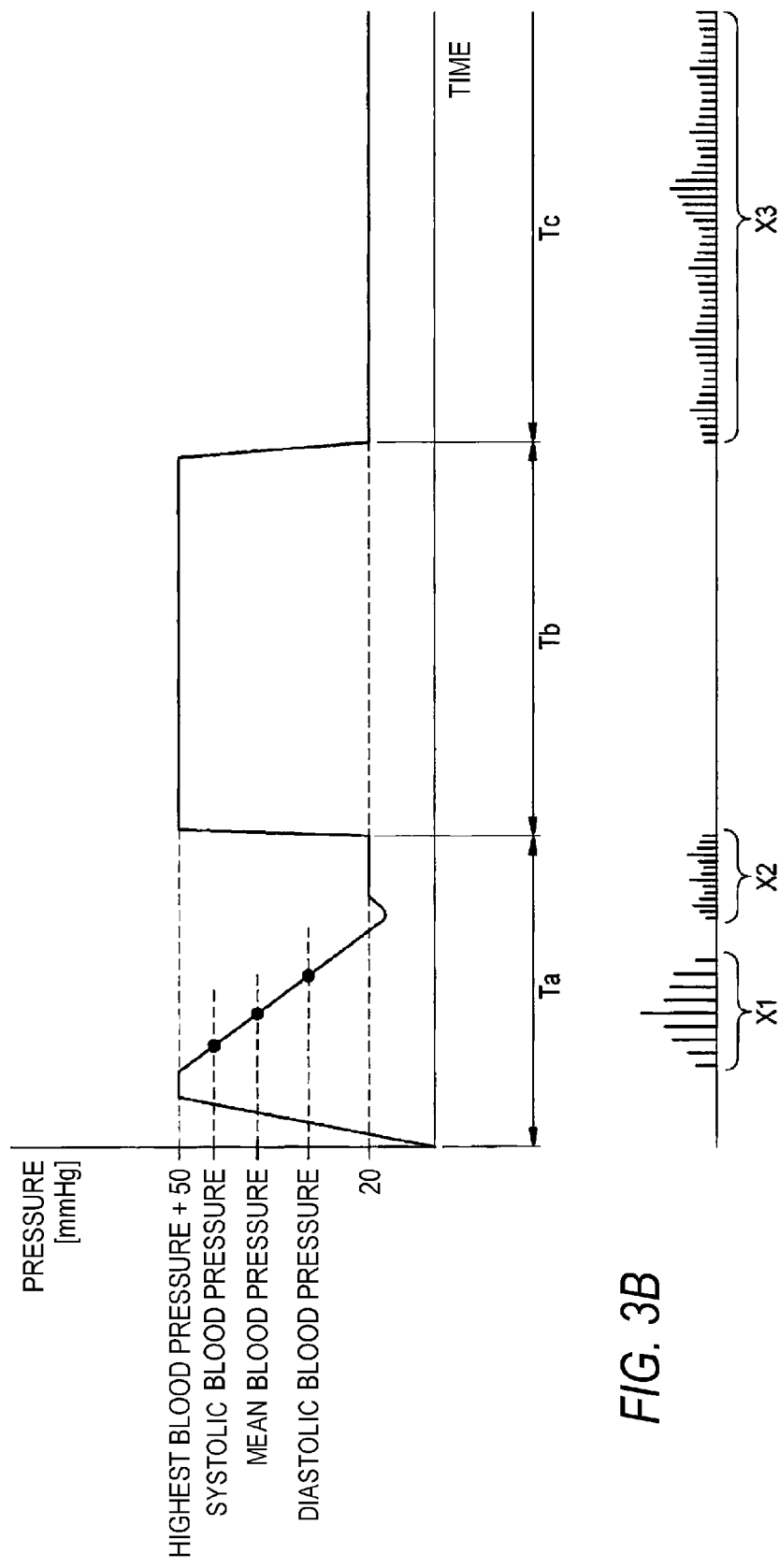

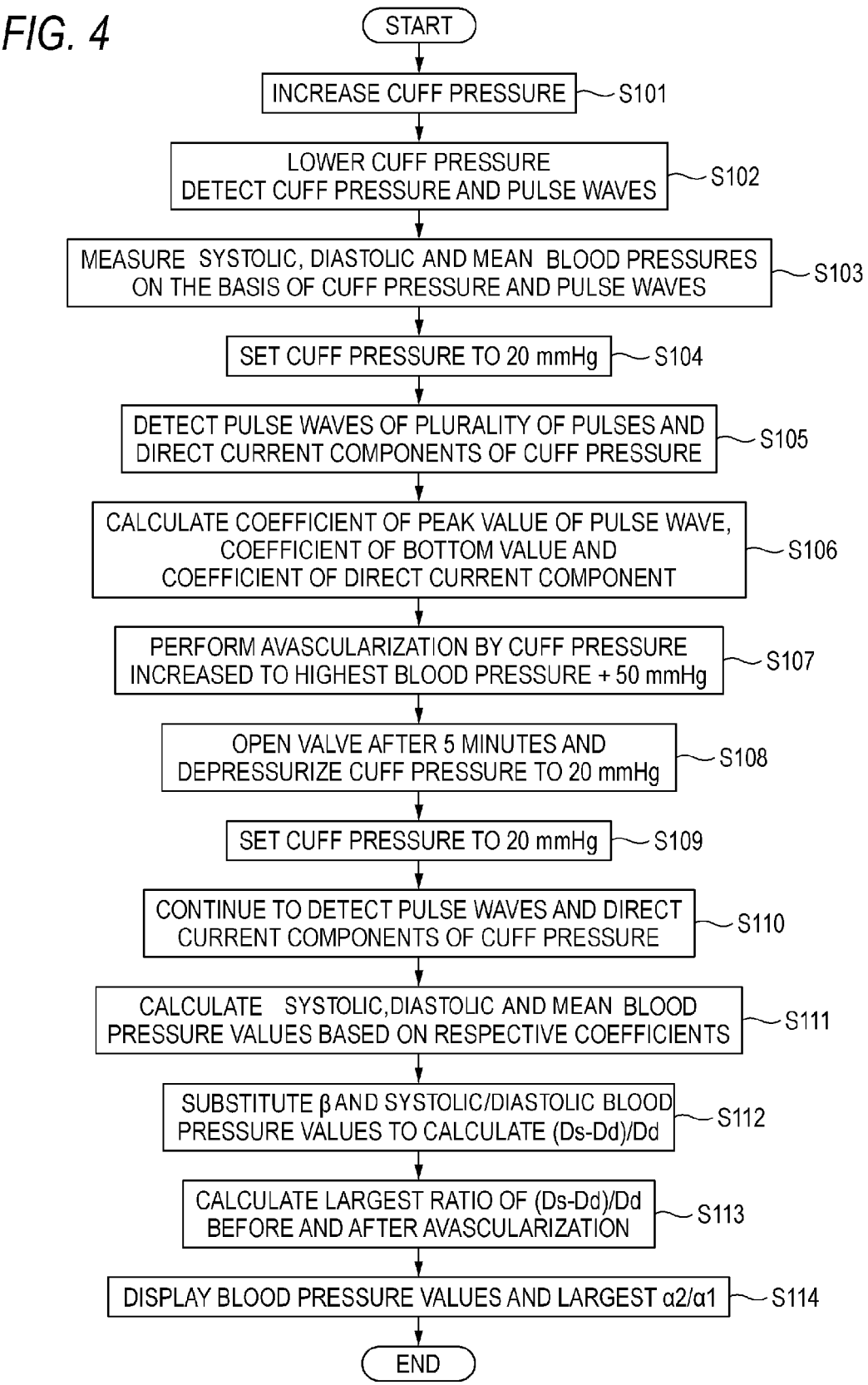

VASCULAR ENDOTHELIAL FUNCTION INSPECTION APPARATUS

CROSS REFERENCE TO RELATED APPLICATION

This application is based on Japanese Patent Applications No. 2014-044125 filed on Mar. 6, 2014, the contents of which are incorporated herein by reference.

BACKGROUND

The presently disclosed subject matter relates an apparatus configured to inspect a vascular endothelial function.

It is said that a decline in vascular endothelial function occurs at an early stage of the arteriosclerosis. Since the decline in vascular endothelial function is reversible, if a decline state in vascular endothelial function can be found at an early stage, the arteriosclerosis may be prevented.

Therefore, for example, JP-A-2011-056200 discloses a vascular endothelial function evaluation apparatus configured to perform pressure stimulation on a body part of a subject for a predetermined time period and to compare pulse waves detected before and after the pressure stimulation, thereby evaluating a vascular endothelial function.

However, according to the vascular endothelial function evaluation apparatus disclosed in JP-A-2011-056200, a personal difference may be caused with respect to the reliability of the evaluation, so that it is required to improve precision of the inspection.

It is therefore an object of the presently disclosed subject matter to provide a vascular endothelial function inspection apparatus capable of improving precision of a vascular endothelial function inspection.

SUMMARY (1) According to an aspect of the invention, a vascular endothelial function inspection apparatus includes a first cuff that is mounted to a first part of a subject, a cuff pressure control unit that controls a pressure applied to the first cuff, a pressure sensor that is connected to the first cuff, a cuff pressure detection unit that detects a cuff pressure from an output of the pressure sensor, a pulse wave detection unit that detects pulse waves from the output of the pressure sensor, a blood pressure measuring unit that measures a blood pressure value based on the cuff pressure and the pulse waves, a storage unit that stores therein an elasticity index value indicating an elasticity of a blood vessel of the subject, and an analysis unit that performs data processing for evaluating an endothelial function of the blood vessel. The cuff pressure control unit applies a continuous pressure to the first part of the subject for a predetermined avascularization time period through the first cuff mounted to the subject, the blood pressure measuring unit calculates blood pressure values of the first part before and after the avascularization time period by using the output of the pressure sensor, and the analysis unit calculates an index, which indicates a change in a blood vessel diameter, before and after the avascularization time period based on the elasticity index value and the blood pressure values measured before and after the avascularization time period, and evaluates a vascular endothelial function of the subject by using the index before the avascularization time period and the index after the avascularization time period.

According to the above configuration (1), the index indicating the change in the blood vessel diameter is calculated using data including the elasticity index value based on hardness of the blood vessel different for each subject, before and after the avascularization time period. In this way, since the vascular endothelial function of the subject is evaluated, also considering a difference in amplitudes of the pulse waves due to the difference in the hardness of the blood vessel, it is possible to correctly inspect the vascular endothelial function for each subject.

(2) In the vascular endothelial function inspection apparatus of (1), the elasticity index value is a value calculated from a relation equation between a blood pressure and a blood vessel diameter and is measured in advance for each subject and is stored in the storage unit.

The elasticity index value is an inherent value to each subject obtained on a basis of a relation equation between the blood pressure and the blood vessel diameter. The elasticity index value is calculated in advance and stored, so that it is possible to more correctly perform the vascular endothelial function inspection for each subject.

(3) In the vascular endothelial function inspection apparatus of (1) or (2), the continuous pressure applied to the first part of the subject for the avascularization time period is higher than the systolic blood pressuresystolic blood pressure of the subject.

According to the above configuration (3), the pressure higher than the systolic blood pressuresystolic blood pressure is applied to the part of the subject, so that it is possible to securely stop the blood from flowing. For this reason, it is possible to correctly calculate the index indicating the change in the blood vessel diameters calculated before and after the avascularization time period, thereby evaluating the vascular endothelial function more correctly.

(4) In the vascular endothelial function inspection apparatus of any one of (1) to (3), the cuff pressure control unit continuously applies a constant pressure lower than the diastolic blood pressure of the subject to the first part after the avascularization time period, and the blood pressure measuring unit measures the blood pressure value after the avascularization time period by using the output of the pressure sensor after the avascularization time period.

According to the above configuration (4), the pressure after the avascularization time period is maintained at the constant pressure lower than the diastolic blood pressure, so that it is possible to continuously measure the blood pressure after the avascularization time period. Thereby, it is possible to continuously observe the change in amplitudes of the pulse waves overlapping with the cuff pressure, thereby evaluating the vascular endothelial function more correctly.

(5) The vascular endothelial function inspection apparatus of any one of (1) to (4) further includes a second cuff that is mounted to a second part of the subject which is different from the first part. The cuff pressure control unit controls a pressure applied to the second cuff so as not to apply the pressure to the second cuff for the avascularization time period, and the analysis unit corrects an index indicating a change in a blood vessel diameter of the first part by using an index indicating a change in a blood vessel diameter of the second part.

According to the above configuration, the blood pressure is measured to calculate the index indicating the change in the blood vessel diameter also for the second part that is not avascularized, and the index is used to correct the index indicating the change in the blood vessel diameter of the first part. Thereby, it is possible to more correctly calculate the change in the blood vessel diameter due to only the influence of pressurization for the avascularization time period. Therefore, it is possible to inspect the vascular endothelial function more correctly.

According to the vascular endothelial function inspection apparatus of the presently disclosed subject matter, it is possible to improve the precision of the vascular endothelial function inspection.

BRIEF DESCRIPTION OF THE DRAWINGS

FIG. 3A illustrates an example of a pressure waveform signal, and FIG. 3B illustrates waveforms of pulse wave components included in the pressure waveform signal.

FIG. 4 is a flowchart showing inspection procedures of a vascular endothelial function.

FIGS. 5A and 5B illustrates a modified embodiment of blood pressure measurement after avascularization, in which FIG. 5A illustrates an example of a pressure waveform signal, and FIG. 5B illustrates waveforms of pulse wave components included in the pressure waveform signal.

DETAILED DESCRIPTION OF EMBODIMENTS

Hereinafter, an illustrative embodiment of the vascular endothelial function inspection apparatus of the presently disclosed subject matter will be described in detail with reference to the drawings.

Figure 1:
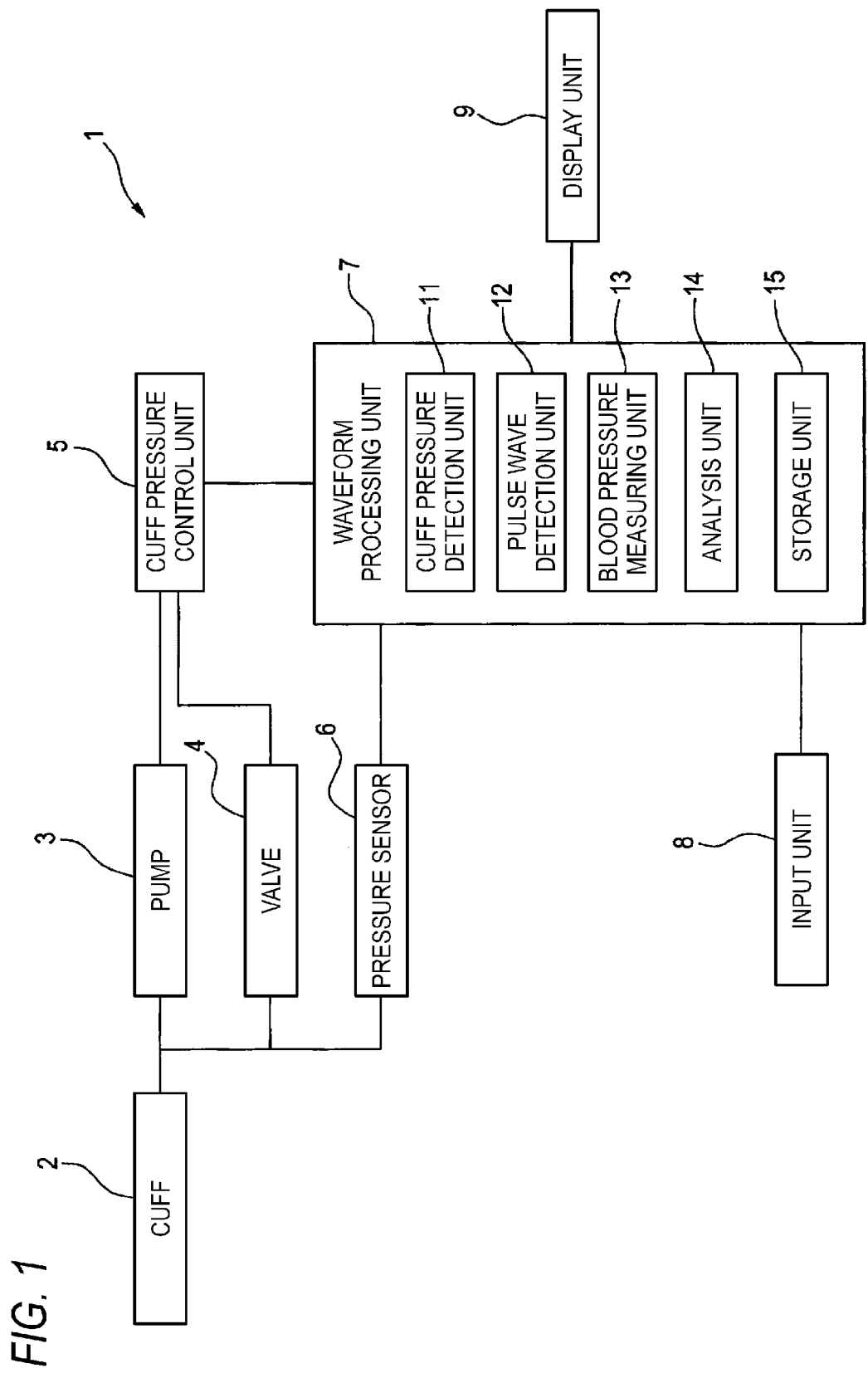
FIG. 1 is a functional block diagram showing a configuration of a vascular endothelial function inspection apparatus according to an illustrative embodiment of the presently disclosed subject matter.
Figure 2:
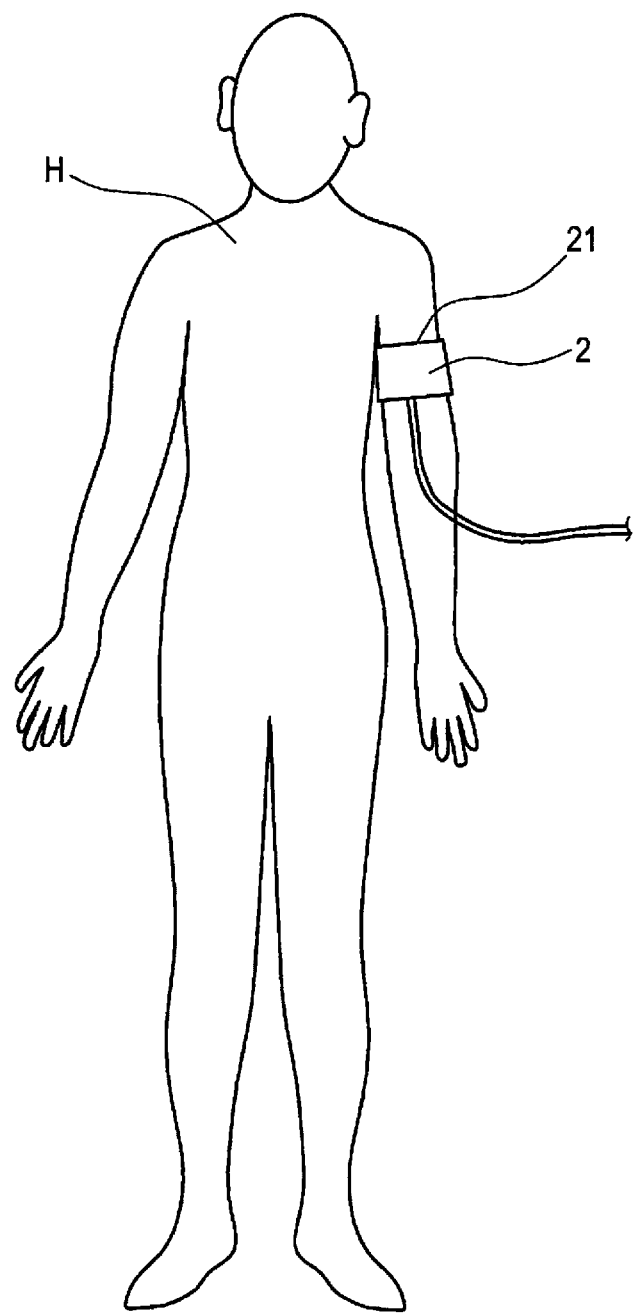
FIG. 2 illustrates an example of a subject having a cuff mounted thereto.

FIG. 1 is a functional block diagram showing a configuration of a vascular endothelial function inspection apparatus 1 according to an illustrative embodiment of the presently disclosed subject matter. FIG. 2 illustrates an example of a subject having a cuff mounted thereto.

As shown in FIG. 1, the vascular endothelial function inspection apparatus 1 has a cuff 2, a pump 3, a valve 4, a cuff pressure control unit 5, a pressure sensor 6, a waveform processing unit 7, an input unit 8 and a display unit 9. Also, the waveform processing unit 7 has a cuff pressure detection unit 11, a pulse wave detection unit 12, a blood pressure measuring unit 13, an analysis unit 14 and a storage unit 15.

The cuff 2 is connected to the pump 3, the valve 4 and the pressure sensor 6. The cuff 2 is configured to be mounted to a part of a living body for which a blood pressure (an arterial pressure) of a subject can be measured, for example, a brachial region (an example of a first part) 21 (refer to FIG. 2). The cuff 2 has a pressure pouch (not shown), and is configured to apply a cuff pressure to the brachial region 21 as the air is blown into the pressure pouch by the pump 3.

The pump 3 is connected to the cuff pressure control unit 5. The pump 3 is configured to blow the air into the pressure pouch of the cuff 2 on the basis of a control signal transmitted from the cuff pressure control unit 5.

The valve 4 is connected to the cuff pressure control unit 5. The valve 4 is configured to switch between an opened state and a closed state so as to exhaust the air from the pressure pouch of the cuff 2 or not to exhaust the air on the basis of a control signal transmitted from the cuff pressure control unit 5.

The cuff pressure control unit 5 is configured to control an air output of the pump 3 and the opening and closing of the valve 4 so that the cuff pressure, which is a pressure of the cuff 2, is pressurized, depressurized or kept at a constant pressure. The cuff pressure control unit 5 is connected in communication with the waveform processing unit 7 and is configured to control the pump 3 and the valve 4 on the basis of a control signal transmitted from the waveform processing unit 7.

The pressure sensor 6 is connected to the cuff 2. When the cuff pressure is applied to the brachial region 21 of the subject H, pulse waves, which are vibrations of a blood vessel wall synchronizing with pulses of the subject H, overlap with the cuff pressure. The pressure sensor 6 is configured to detect a pressure waveform signal of which the pulse waves overlap with the cuff pressure, and to transmit the detected pressure waveform signal to the waveform processing unit 7.

The waveform processing unit 7 is configured to analyze the pressure waveform signal output from the pressure sensor 6. The waveform processing unit 7 is a calculation processing circuit including a calculation device such as a CPU. The operations of the respective units in the vascular endothelial function inspection apparatus 1 can be implemented by operations of hardware such as a circuit device and the like arranged on a substrate of the waveform processing unit 7, operations of software such as a program and the like stored in the calculation device or a combination thereof. The waveform processing unit 7 is configured to function as the cuff pressure detection unit 11, the pulse wave detection unit 12, the blood pressure measuring unit 13, the analysis unit 14 and the storage unit 15.

The cuff pressure detection unit 11 is configured to analyze the pressure waveform signal output from the pressure sensor 6, thereby detecting the cuff pressure of the cuff 2.

The pulse wave detection unit 12 is configured to analyze the pressure waveform signal output from the pressure sensor 6, thereby detecting the pulse waves overlapping with the cuff pressure of the cuff 2.

The blood pressure measuring unit 13 is configured to measure blood pressure values of the subject H on the basis of the cuff pressure detected in the cuff pressure detection unit 11 and the pulse waves detected in the pulse wave detection unit 12. The blood pressure values include the systolic blood pressuresystolic blood pressure value, the diastolic blood pressure value and an mean blood pressure value, for example.

The analysis unit 14 is configured to perform an analysis for evaluating the vascular endothelial function of the subject H by using the blood pressure value measured in the blood pressure measuring unit 13, data stored in the storage unit 15, and the like.

The storage unit 15 is configured to store therein the blood pressure value measured in the blood pressure measuring unit 13, an elasticity index value $\beta$ indicating an elasticity (hardness) of a blood vessel calculated in advance for each subject, coefficient values obtained for continuously calculating a blood pressure, data analyzed in the analysis unit 14, and the like.

The input unit 8 is configured to input the elasticity index value $\beta$ calculated in advance for each subject and the like to the storage unit 15 of the waveform processing unit 7 from an outside. The input unit 8 is composed of a keyboard, a touch panel and the like, for example.

The display unit 9 is configured to display an inspection result of the vascular endothelial function, the measured blood pressure values and the like. The display unit 9 is composed of a touch panel-type liquid crystal screen, for example, and is configured to operate in accordance with a display control signal output from the waveform processing unit 7.

Subsequently, operations of the vascular endothelial function inspection apparatus 1 are described with reference to FIGS. 3 and 4. FIG. 3A illustrates an example of a pressure waveform signal, and FIG. 3B illustrates waveforms of pulse wave components included in the pressure waveform signal.

(Calculation of Elasticity Index Value)

In the vascular endothelial function inspection of this illustrative embodiment, the elasticity index value β indicating the elasticity of the blood vessel of the subject H is first calculated in advance. The elasticity index value β can be expressed by a following equation 1, for example.

$$\beta = \ln(Ps/Pd)/[(Ds-Dd)/Dd] \quad \text{[equation 1]}$$

Ps: systolic blood pressure value
(the systolic blood pressuresystolic blood pressure value)
Pd: diastolic blood pressure value
(the diastolic blood pressure value)
Ds: maximum blood vessel diameter in systole
Dd: minimum blood vessel diameter in diastole In the equation 1, the elasticity index value β indicating the elasticity of the blood vessel is defined by a relation equation of the blood pressure value and the blood vessel diameter.

First, the systolic blood pressuresystolic blood pressure value (Ps) and the diastolic blood pressure value (Pd) of the subject H at a normal state are measured using a blood pressure meter. Also, the maximum blood vessel diameter (Ds) and the minimum blood vessel diameter (Dd) are measured using an ultrasonic inspection method, for example. The elasticity index value β is calculated using the measured systolic blood pressuresystolic blood pressure value (Ps), diastolic blood pressure value (Pd), maximum blood vessel diameter (Ds) and minimum blood vessel diameter (Dd) and the equation 1. The elasticity index value β is an inherent value determined by the hardness of the blood vessel of the subject H. The calculated elasticity index value β is stored in the storage unit 15 of the waveform processing unit 7 through the input unit 8.

Subsequently, after the cuff 2 is mounted to the brachial region 21 of the subject H, each processing shown in FIG. 4 is performed.

(Measurement of Blood Pressure and Calculation of Coefficient)

A reference numeral Ta in FIG. 3A indicates a blood pressure measurement time period. Also, reference numerals X1, X2 in FIG. 3B indicate pulse waves detected from a pressure signal waveform during the blood pressure measurement time period.

In order to measure the blood pressure, the cuff pressure control unit 5 closes the valve 4 and blows the air into the cuff 2 from the pump 3, thereby pressurizing and increasing the cuff pressure (step S101).

After the cuff pressure reaches a predetermined pressure (a pressure higher than the maximum blood pressure value), the cuff pressure control unit 5 stops the air flowing to the cuff 2 from the pump 3 and opens the valve 4. Thereby, the cuff pressure is depressurized and lowered. During the depressurization time period, the pressure sensor 6 detects the pressure waveform signal of which the pulse waves overlap with the cuff pressure and transmits the same to the waveform processing unit 7. From the pressure waveform signal, the cuff pressure is detected by the cuff pressure detection unit 11. Also, from the pressure waveform signal, the pulse wave X1 is detected by the pulse wave detection unit 12 (step S102).

The blood pressure measuring unit 13 measures the systolic blood pressure value (Ps), the diastolic blood pressure value (Pd) and an mean blood pressure value, based on the detected cuff pressure and a change in amplitude of the pulse wave X1 (step S103). The measured blood pressure values are stored in the storage unit 15.

Thereafter, the cuff pressure control unit 5 closes the valve 4 and controls the pump 3 so that the cuff pressure is kept at a pressure (for example, 20 mmHg) lower than the diastolic blood pressure value (step S104). At this control state, the pulse wave X2 overlapping with the cuff pressure is detected for each pulse by the pulse wave detection unit 12, and a direct current component of the cuff pressure in each of the detected pulse waves X2 is detected by the cuff pressure detection unit 11 (step S105). The blood pressure measuring unit 13 averages the pulse waves of the plurality of pulses and calculates a peak value and a bottom value of the averaged pulse wave. Also, the blood pressure measuring unit 13 calculates an average direct current component, which is an average of the direct current components of the cuff pressure. The blood pressure measuring unit 13 calculates a coefficient A, which associates the peak value of the pulse wave X2 with the systolic blood pressure value measured in step S103, a coefficient B, which associates the bottom value of the pulse wave X2 with the diastolic blood pressure value, and a coefficient C, which associates the average direct current component with the mean blood pressure value (step S106).

(Avascularization for Stimulating Vascular Endothelial)

A reference numeral Tb in FIG. 3A indicates an avascularization time period of avascularization for stimulating the vascular endothelial.

In order to simulate the vascular endothelial, the avascularization is performed for the brachial region 21 by the cuff 2. The cuff pressure control unit 5 blows the air into the cuff 2 from the pump 3, thereby increasing the cuff pressure. The cuff pressure for avascularization is set as a summed pressure of the systolic blood pressure value and a predetermined pressure (for example, +50 mmHg) (step S107). The cuff pressure control unit 5 controls the pressure for avascularization to be continuously maintained for the predetermined avascularization time period Tb (for example, about 5 minutes).

(Blood Pressure Measurement after Avascularization)

A reference numeral Tc in FIG. 3A indicates a blood pressure measurement time period after the avascularization for stimulating the vascular endothelial.

The cuff pressure control unit 5 opens the valve 4 after the predetermined avascularization time period Tb elapses, and depressurizes the cuff pressure to lower the cuff pressure to a predetermined pressure (for example, 20 mmHg) lower than the diastolic blood pressure value (step S108).

Subsequently, the cuff pressure control unit 5 closes the valve 4 to control the pump 3 so that the cuff pressure is maintained at 20 mmHg (step S109). At this control state, the pulse waves X3 overlapping with the cuff pressure are continuously sequentially detected by the pulse wave detection unit 12, and direct current components of the cuff pressure in the detected pulse wave components X3 are detected by the cuff pressure detection unit 11 (step S110). The blood pressure measuring unit 13 continues to measure the systolic blood pressure value and the diastolic blood pressure value after the avascularization by each of the detected pulse waves X3 and the coefficients A, B calculated in step S106 and the mean blood pressure value by the direct current components of the cuff pressure and the coefficient C (step S111).

(Analysis for Evaluation of Vascular Endothelial Function)

The analysis unit 14 substitutes the elasticity index value $\beta$ calculated in advance, the systolic blood pressure value (Ps) and the diastolic blood pressure value (Pd) in the equation 1, thereby calculating a value (also referred to as elasticity extension value $\alpha$) of the index ((Ds−Dd)/Dd) indicating a change in the blood vessel diameter (step S112).

For example, the analysis unit 14 substitutes the elasticity index value $\beta$, and the systolic blood pressure value (Ps) and diastolic blood pressure value (Pd) before the avascularization, which are measured in step S103, in the equation 1, thereby calculating an elasticity extension value $\alpha 1$ before the avascularization, which is an index indicating a change in the blood vessel diameter before the avascularization (step S112).

Likewise, the analysis unit 14 substitutes the elasticity index value $\beta$, and the systolic blood pressure value and diastolic blood pressure value after the avascularization, which are continuously measured in step S111, in the equation 1, thereby calculating an elasticity extension value $\alpha 2$ after the avascularization. The elasticity extension value $\alpha 2$ after the avascularization is continuously calculated, like the calculation of each blood pressure value in step S111.

The analysis unit 14 calculates ratios $\alpha 2/\alpha 1$ of the elasticity extension value $\alpha 1$ before the avascularization and the respective elasticity extension values $\alpha 2$ after the avascularization, for example, and obtains the largest ratio $\alpha 2/\alpha 1$ (step S113). The respective values calculated in steps S111 to S113 are stored in the storage unit 15.

The respective blood pressure values before and after the avascularization, the largest ratio $\alpha 2/\alpha 1$ and the like measured in this way are displayed on the display unit 9 of the vascular endothelial function inspection apparatus 1, as inspection results of the vascular endothelial function (step S114). Thereby, the processing is over.

In general, it is said that the vascular endothelial function is favorable if a value FMD (=(the maximum blood vessel diameter after the avascularization is released−the blood vessel diameter at rest)/the blood vessel diameter at rest× 100) [%] indicating a change ratio of the blood vessel diameter by the avascularization exceeds 7 to 8%. Therefore, a correlation between the largest ratio $\alpha 2/\alpha 1$ calculated as described above and an FMD value is obtained in advance, and the vascular endothelial function for the calculated largest ratio $\alpha 2/\alpha 1$ is evaluated on the basis of the correlation.

In the related art, when evaluating the vascular endothelial function by using the pulse waves before and after the pressurization, the maximum amplitudes of the pulse waves before and after the pressurization are compared, as disclosed in JP-A-2011-056200. However, since the elasticity (hardness) of the blood vessel of the subject is different for each subject, there is a possibility that a difference will be caused in amplitudes of measured pulse waves due to the difference of the hardness of the blood vessel.

In contrast, according to the vascular endothelial function inspection apparatus 1 of this illustrative embodiment, the elasticity index value $\beta$ based on the hardness of the blood vessel different for each subject is obtained in advance. Then, the elasticity extension value $\alpha$ (=(Ds−Dd)/Dd) indicating the change in the blood vessel diameter is respectively calculated before and after the avascularization time period Tb by using the data including the elasticity index value $\beta$. Then, the ratios $\alpha 2/\alpha 1$ of the elasticity extension value $\alpha 1$ before the avascularization and the respective elasticity extension values $\alpha 2$ after the avascularization are calculated and the comparison thereof is displayed as an example of the evaluation result of the vascular endothelial function of the subject. In this way, since the vascular endothelial function of the subject is evaluated, considering the difference in the amplitudes of the pulse waves due to the difference in the hardness of the blood vessel, it is possible to correctly inspect the vascular endothelial function for each subject.

Also, a correlation between the ratio $\alpha 2/\alpha 1$ of the elasticity extension values before and after the avascularization time period and the FMD value (=(the maximum blood vessel diameter after the avascularization is released−the blood vessel diameter at rest)/the blood vessel diameter at rest×100) [%] may be obtained in advance. According to this configuration, not only the healthcare professional but also the subject who receives an explanation can easily recognize the evaluation result of the vascular endothelial function.

Also, the elasticity index value $\beta$ is expressed by the equation $\beta=\ln(Ps/Pd)/[(Ds-Dd)/Dd]$ and is an inherent value to each subject obtained on the basis of a relation equation between the blood pressure value of the subject and the blood vessel diameter. By using the elasticity index value $\beta$ to calculate the elasticity extension value $\alpha(=(Ds-Dd)/Dd)$ indicating the change in the blood vessel diameter, it is possible to obtain the correct change in the blood vessel diameter for each subject, so that it is possible to perform the vascular endothelial function inspection having higher reliability.

Also, the cuff pressure applied for avascularization is set to the pressure (for example, 50 mmHg) higher than the systolic blood pressure of the subject by a predetermined value. Thereby, it is possible to securely avascularize the blood flow in the artery of the brachial region 21 and to more correctly calculate the change in the blood vessel diameter from the blood pressure values measured before and after the avascularization.

Also, it is possible to continuously measure the blood pressure values after the avascularization by maintaining the cuff pressure after the avascularization to the constant pressure lower than the diastolic blood pressure value. Thereby, since it is possible to continuously observe the change in the amplitudes of the pulse waves overlapping with the cuff pressure, it is possible to inspect the vascular endothelial function more correctly.

In the meantime, the presently disclosed subject matter is not limited to the above illustrative embodiment and can be appropriately modified and improved. In addition, the materials, shapes, sizes, numerical values, forms, number, arrangement places and the like of the respective constitutional elements of the above illustrative embodiment are arbitrary and are not particularly limited inasmuch as the presently disclosed subject matter can be implemented.

Figures 5A, 5B:
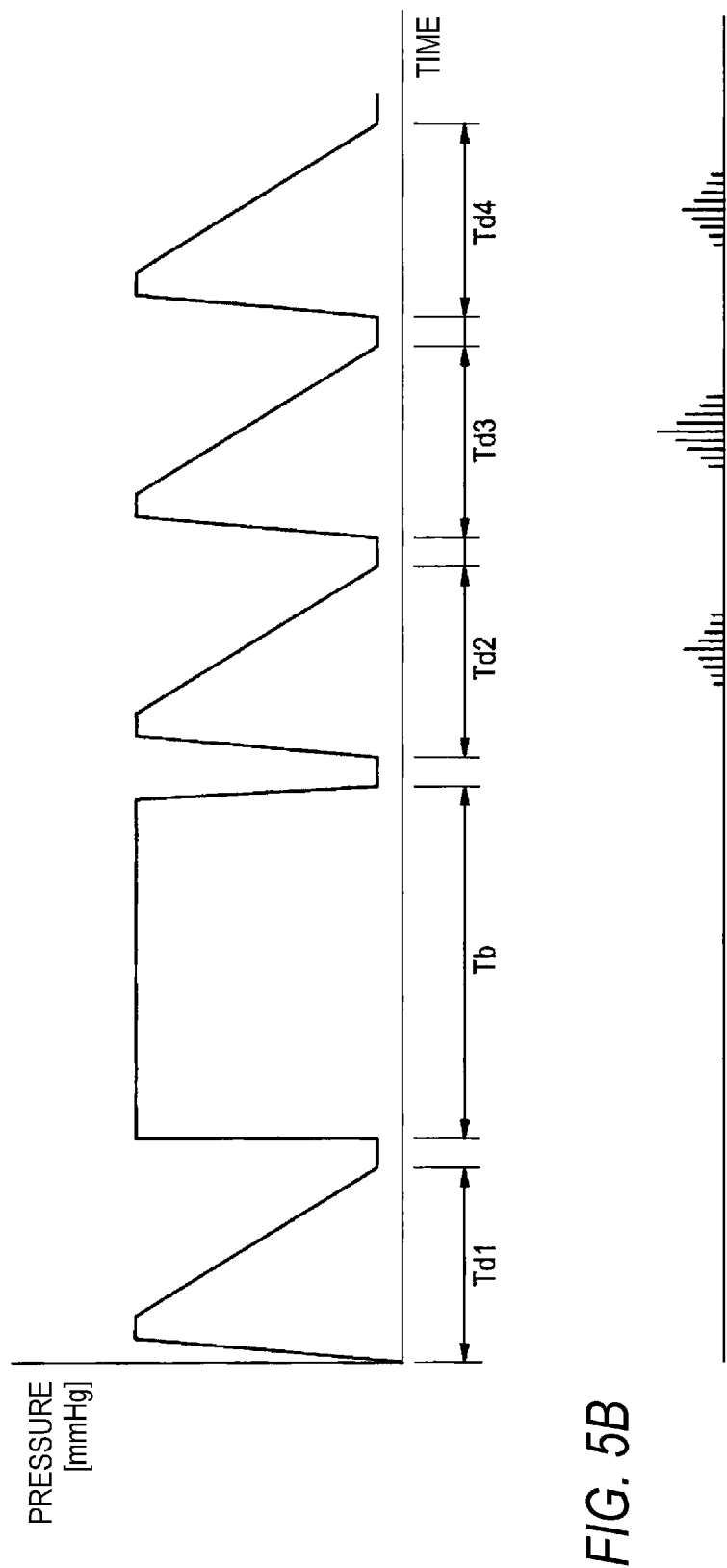

For example, in the above illustrative embodiment, the blood pressure values are continuously measured with the cuff pressure after the avascularization being maintained at the constant pressure lower than the diastolic blood pressure value. However, the presently disclosed subject matter is not limited thereto. For example, as shown in FIG. 5, the blood pressure values after the avascularization may be intermittently measured.

Specifically, the blood pressure values of the subject H at a normal state before the avascularization for evaluation of the vascular endothelial function are measured by the blood pressure measuring unit 13 for a depressurization time period indicated with a time period Td1. Subsequently, the brachial region 21 is continuously avascularized for predetermined time, as shown with a time period Tb. Then, the cuff pressure is pressurized and depressurized to measure the blood pressure values in each of time periods Td2 to Td4 after the avascularization, like the time period Td1. Then, the elasticity extension values α may be calculated using the blood pressure values after the avascularization intermittently measured in this way and the elasticity index value β calculated in advance, like the above illustrative embodiment.

Figure 6:
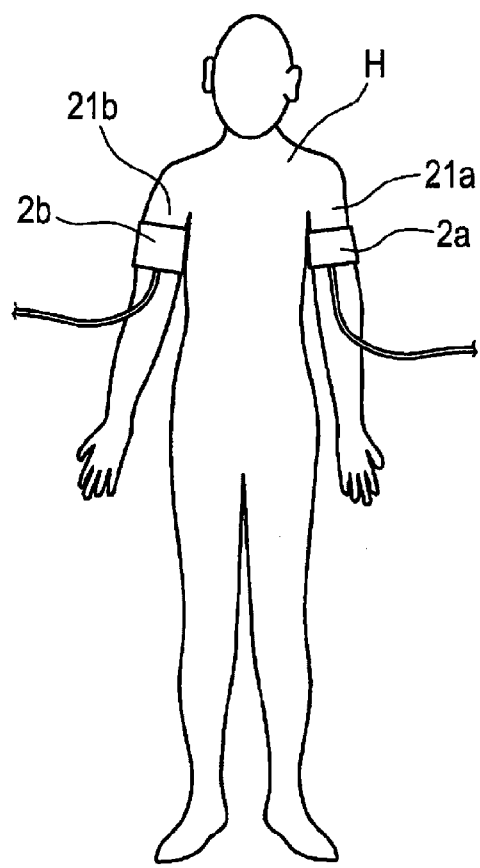
FIG. 6 illustrates an example where another cuff is mounted on another arm other than the arm to which the cuff is mounted, which is shown in FIG. 2.

Also, as shown in FIG. 2, the example where the one cuff 2 is mounted to the subject H during the inspection has been described. However, two cuffs 2a, 2b may be mounted, as shown in FIG. 6.

The cuff 2a (an example of the first cuff) and the cuff 2b (an example of the second cuff) are mounted to different arms of the subject H. The cuff 2a is mounted to a brachial region 21a (an example of the first part) of the subject H and is used in the same manner as the cuff 2 described in the above illustrative embodiment. In contrast, the cuff 2b is mounted to a brachial region 21b (an example of the second part) different from the brachial region 21a to which the cuff 2a is mounted, and is used as a cuff for correcting an amplitude of a pulse wave to be detected. The cuffs 2a, 2b have the same configuration as the cuff 2 shown in FIG. 1 and are connected to the waveform processing unit 7.

Figure 7:
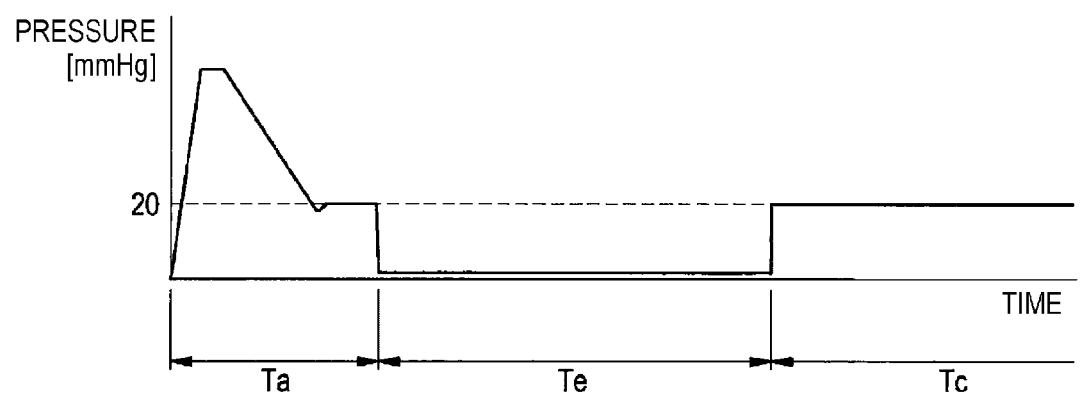
FIG. 7 illustrates an example of a pressure waveform signal measured at the separate cuff shown in FIG. 6.

During the inspection, the cuff pressure of the cuff 2b is controlled by the cuff pressure control unit 5, as shown in FIG. 7. The cuff pressure for time periods Ta, Tc is controlled in the same manner as the cuff pressure for time periods Ta, Tc shown in FIG. 3. In contrast, the cuff pressure for a time period Te is controlled to a substantial zero pressure. That is, during the time period Te, the high cuff pressure for avascularization, like the cuff pressure for the time period Tb shown in FIG. 3, is not applied to the brachial region 21b. In the meantime, the starting and ending timings of the pressurization/depressurization of the cuff 2a and the cuff 2b controlled in the inspection process are the same, and a length of the time period Te is the same as that of the time period Tb shown in FIG. 3.

During the process where the cuff pressure of the cuff 2b is controlled in this way, the systolic blood pressure value, the diastolic blood pressure value and the mean blood pressure value are measured for the depressurization time period Ta by the blood pressure measuring unit 13, based on the cuff pressure detected from the cuff 2b and the change in amplitude of the pulse wave. Also, during the time period Tc, the pulse waves overlapping with the cuff pressure of the cuff 2b are continuously sequentially detected by the pulse wave detection unit 12, and the direct current components of the cuff pressure in the detected pulse waves are detected by the cuff pressure detection unit 11. The blood pressure measuring unit 13 continues to measure the systolic blood pressure value, the diastolic blood pressure value and the mean blood pressure value by the detected pulse wave components and direct current components of the cuff pressure and the coefficients A to C (refer to step S106 in the above illustrative embodiment).

The analysis unit 14 calculates an elasticity extension value $α3$ for the time period Ta and respective elasticity extension values $α4$ for the time period Tc, thereby calculating the largest ratio $α4/α3$. The analysis unit 14 subtracts the ratio $α4/α3$ obtained from the cuff 2b from the ratio $α2/α1$ obtained from the cuff 2a.

When the high cuff pressure for avascularization is applied to the brachial region 21a continuously for a predetermined time period by the cuff 2a, the elasticity extension value α calculated on the basis of the signal detected from the cuff 2a may include not only a change in the blood vessel diameter due to only the cuff pressure applied for avascularization but also a variation due to a change in the blood pressure resulting from a difference of measuring time, a variation due to disturbance of the autonomic nerve, and the like. Therefore, as described above, the blood pressure values are measured to calculate the elasticity extension values $α3$, $α4$ also for the brachial region 21b to which the high cuff pressure for avascularization is not applied, and the elasticity extension values of the avascularized brachial region 21a and the non-avascularized brachial region 21b are compared. Thereby, it is possible to perform correction for removing a variation of the blood pressure, an influence of the autonomic nerve, and the like, so that it is possible to more correctly calculate the change in the blood vessel diameter due to only the influence of avascularization.

Also, for example, in the example described in FIGS. 1 to 4, the disturbance of the autonomic nerve of the subject may be detected and the correction for removing the change in the blood vessel diameter due to the disturbance may be performed. Specifically, a pulse interval is detected on the basis of the waveform of the pulse waves detected in the pulse wave detection unit 12 through the analysis of the analysis unit 14. The detection is respectively performed when measuring the blood pressure value before and after the avascularization. The analysis unit 14 is configured to calculate a standard deviation of the pulse intervals and to determine whether or not the disturbance of the autonomic nerve on the basis of the standard deviation. When it is determined that there is the disturbance of the autonomic nerve, the analysis unit performs correction for subtracting a variation of the blood vessel diameter resulting from the disturbance from the elasticity extension value α and removing the same. For the correction, a correlation between the change in the pulse interval and the change amount of the blood vessel diameter is obtained in advance and stored in the storage unit 15.

When the body of the subject is applied with the stimulus, the sympathetic nerve actively operates, thereby changing the pulse interval. For this reason, it is possible to detect whether the disturbance is caused in the balance of the operation of the sympathetic nerve by observing the pulse interval. When the balance of the sympathetic nerve is disturbed, it also influences the blood flow, resulting in the change in the blood vessel diameter. Therefore, it is possible to check that the variation of the blood vessel diameter due to the disturbance of the autonomic nerve is included in the change in the blood vessel diameter by detecting the change in the pulse interval before and after the avascularization. Thereby, it is possible to correct and remove the variation of the blood vessel diameter due to the disturbance of the autonomic nerve, so that it is possible to more correctly calculate the change in the blood vessel diameter resulting from the avascularization.

What is claimed is:

1. A vascular endothelial function inspection apparatus comprising:
- a first cuff that is configured to be attached to a first part of a subject;
- a cuff pressure control unit that controls a pressure applied to the first cuff;
- a pressure sensor that is connected to the first cuff;
- a cuff pressure detection unit that detects a cuff pressure from an output of the pressure sensor;
- a pulse wave detection unit that detects pulse waves from the output of the pressure sensor;
- a blood pressure measuring unit that measures a blood pressure value based on the cuff pressure and the pulse waves;
- a storage unit that stores therein an elasticity index value indicating an elasticity of a blood vessel of the subject; and
- an analysis unit that performs data processing for evaluating an endothelial function of the blood vessel,
- wherein the cuff pressure control unit applies a continuous pressure to the first part of the subject for a predetermined avascularization time period through the first cuff mounted to the subject,
- wherein the blood pressure measuring unit calculates blood pressure values of the first part before and after the avascularization time period by using the output of the pressure sensor, and
- wherein the analysis unit calculates an index, which indicates a change in a blood vessel diameter, before and after the avascularization time period based on the elasticity index value and the blood pressure values measured before and after the avascularization time period, and evaluates a vascular endothelial function of the subject by using the index before the avascularization time period and the index after the avascularization time period.

2. The vascular endothelial function inspection apparatus according to claim 1, wherein the elasticity index value is a value calculated from a relation equation between a blood pressure and a blood vessel diameter and is measured in advance for each subject and is stored in the storage unit.

3. The vascular endothelial function inspection apparatus according to claim 2, wherein the continuous pressure applied to the first part of the subject for the avascularization time period is higher than a systolic blood pressure of the subject.

4. The vascular endothelial function inspection apparatus according to claim 3, wherein the cuff pressure control unit continuously applies a constant pressure lower than a diastolic blood pressure of the subject to the first part after the avascularization time period, and
- wherein the blood pressure measuring unit measures the blood pressure value after the avascularization time period by using the output of the pressure sensor after the avascularization time period.

5. The vascular endothelial function inspection apparatus according to claim 4, further comprising a second cuff that is configured to be attached to a second part of the subject which is different from the first part,
- wherein the cuff pressure control unit controls a pressure applied to the second cuff so as not to apply the pressure to the second cuff for the avascularization time period, and
- wherein the analysis unit corrects an index indicating a change in a blood vessel diameter of the first part by using an index indicating a change in a blood vessel diameter of the second part.

6. The vascular endothelial function inspection apparatus according to claim 3, further comprising a second cuff that is configured to be attached to a second part of the subject which is different from the first part,
- wherein the cuff pressure control unit controls a pressure applied to the second cuff so as not to apply the pressure to the second cuff for the avascularization time period, and
- wherein the analysis unit corrects an index indicating a change in a blood vessel diameter of the first part by using an index indicating a change in a blood vessel diameter of the second part.

7. The vascular endothelial function inspection apparatus according to claim 2, wherein the cuff pressure control unit continuously applies a constant pressure lower than a diastolic blood pressure of the subject to the first part after the avascularization time period, and
- wherein the blood pressure measuring unit measures the blood pressure value after the avascularization time period by using the output of the pressure sensor after the avascularization time period.

8. The vascular endothelial function inspection apparatus according to claim 7, further comprising a second cuff that is configured to be attached to a second part of the subject which is different from the first part,
- wherein the cuff pressure control unit controls a pressure applied to the second cuff so as not to apply the pressure to the second cuff for the avascularization time period, and
- wherein the analysis unit corrects an index indicating a change in a blood vessel diameter of the first part by using an index indicating a change in a blood vessel diameter of the second part.

9. The vascular endothelial function inspection apparatus according to claim 2, further comprising a second cuff that is configured to be attached to a second part of the subject which is different from the first part,
- wherein the cuff pressure control unit controls a pressure applied to the second cuff so as not to apply the pressure to the second cuff for the avascularization time period, and
- wherein the analysis unit corrects an index indicating a change in a blood vessel diameter of the first part by using an index indicating a change in a blood vessel diameter of the second part.

10. The vascular endothelial function inspection apparatus according to claim 1, wherein the continuous pressure applied to the first part of the subject for the avascularization time period is higher than a systolic blood pressure of the subject.

11. The vascular endothelial function inspection apparatus according to claim 10, wherein the cuff pressure control unit continuously applies a constant pressure lower than a diastolic blood pressure of the subject to the first part after the avascularization time period, and
- wherein the blood pressure measuring unit measures the blood pressure value after the avascularization time period by using the output of the pressure sensor after the avascularization time period.

12. The vascular endothelial function inspection apparatus according to claim 11, further comprising a second cuff that is configured to be attached to a second part of the subject which is different from the first part, wherein the cuff pressure control unit controls a pressure applied to the second cuff so as not to apply the pressure to the second cuff for the avascularization time period, and wherein the analysis unit corrects an index indicating a change in a blood vessel diameter of the first part by using an index indicating a change in a blood vessel diameter of the second part.

13. The vascular endothelial function inspection apparatus according to claim 10, further comprising a second cuff that is configured to be attached to a second part of the subject which is different from the first part, wherein the cuff pressure control unit controls a pressure applied to the second cuff so as not to apply the pressure to the second cuff for the avascularization time period, and wherein the analysis unit corrects an index indicating a change in a blood vessel diameter of the first part by using an index indicating a change in a blood vessel diameter of the second part.

14. The vascular endothelial function inspection apparatus according to claim 1, wherein the cuff pressure control unit continuously applies a constant pressure lower than a diastolic blood pressure of the subject to the first part after the avascularization time period, and wherein the blood pressure measuring unit measures the blood pressure value after the avascularization time period by using the output of the pressure sensor after the avascularization time period.

15. The vascular endothelial function inspection apparatus according to claim 14, further comprising a second cuff that is configured to be attached to a second part of the subject which is different from the first part, wherein the cuff pressure control unit controls a pressure applied to the second cuff so as not to apply the pressure to the second cuff for the avascularization time period, and wherein the analysis unit corrects an index indicating a change in a blood vessel diameter of the first part by using an index indicating a change in a blood vessel diameter of the second part.

16. The vascular endothelial function inspection apparatus according to claim 1, further comprising a second cuff that is configured to be attached to a second part of the subject which is different from the first part, wherein the cuff pressure control unit controls a pressure applied to the second cuff so as not to apply the pressure to the second cuff for the avascularization time period, and wherein the analysis unit corrects an index indicating a change in a blood vessel diameter of the first part by using an index indicating a change in a blood vessel diameter of the second part.

\* \* \* \* \*